United States Patent [19]

Iwakoshi et al.

[11] Patent Number: 4,973,311
[45] Date of Patent: Nov. 27, 1990

[54] ASPIRATOR FOR ENDOSCOPIC SYSTEM

[75] Inventors: Keiichi Iwakoshi, Nasu; Mitsuru Sato, Shibuya; Hiroyuki Umeda, Kasukabe; Toshinori Nishizawa, Mitaka, all of Japan

[73] Assignees: Kabushiki Kaisha Toshiba, Kawasaki; Kabushiki Kaisha Machidaseisakujyo, Tokyo, both of Japan

[21] Appl. No.: 138,074

[22] Filed: Dec. 28, 1987

[30] Foreign Application Priority Data

Dec. 27, 1986 [JP] Japan .............................. 61-311891

[51] Int. Cl.⁵ .............................................. A61M 1/00
[52] U.S. Cl. ...................................... 604/119; 604/35; 128/4
[58] Field of Search .......................... 604/27, 30-35, 604/65, 67, 93, 43, 118, 119, 120, 317, 319, 320; 128/4-11

[56] References Cited

U.S. PATENT DOCUMENTS

| | | | |
|---|---|---|---|
| 3,659,605 | 5/1972 | Sielaff | 604/65 |
| 3,812,855 | 5/1974 | Banko | 604/120 |
| 3,885,567 | 5/1975 | Ross | 604/120 |
| 3,924,608 | 12/1975 | Mitsui | 128/6 |
| 3,955,574 | 5/1976 | Rubinstein | 604/151 |
| 4,052,987 | 10/1977 | Wuchinich et al. | 604/65 |
| 4,146,019 | 3/1979 | Bass et al. | 604/37 |
| 4,274,411 | 6/1981 | Dotson, Jr. | 604/120 |
| 4,303,072 | 12/1981 | Lewis | 604/119 |
| 4,402,310 | 9/1983 | Kimura | 604/35 |
| 4,710,165 | 12/1987 | McNeil et al. | 604/67 |

*Primary Examiner*—C. Fred Rosenbaum
*Assistant Examiner*—Denise W. DeFranco
*Attorney, Agent, or Firm*—Foley & Lardner, Schwartz, Jeffery, Schwaab, Mack, Blumenthal & Evans

[57] ABSTRACT

An aspirator for an endoscopic system has a suction nozzle for aspirating obstacles and disposed at an end of an endoscope, a suction pump, a suction flask for receiving the aspirated obstacles, and a suction conduit for connecting the suction nozzle to the suction pump via the suction flask. The aspirator further comprises an electromagnetic valve disposed in the suction conduit, and an electromagnetic valve controller. The electromagnetic controller controls the electromagnetic valve such that the suction conduit is closed when an aspiration command signal is not supplied from an aspirator button during the operation of the suction pump, and such that the suction conduit is alternately opened and closed when the aspiration command signal is supplied from the aspirator button during the operation of the suction pump.

2 Claims, 8 Drawing Sheets

ASPIRATOR FOR ENDOSCOPIC SYSTEM

BACKGROUND OF THE INVENTION

1. Field of the Invention

The present invention relates to an aspirator for a medical electronic endoscopic system, and particularly to an aspirator which is used for an endoscope system and able to perform an automatic intermittent aspirating operation.

2. Description of the Prior Art

Endoscopic systems are widely used for inspecting and treating subjects such as the duodenum, the rectum, the large intestine, the esophagus, the ear, the nose, the bladder, etc., of a body.

An aspirator for the endoscopic system keeps the view field of an optical observation system disposed at a front end of the endoscope clean during the operation.

Particularly, when the endoscope is used to inspect and treat an affected part on a digestive system of the body, obstacles such as mucus, vegetable residues and feculence around the subject may hinder the view field of the optical observation system so that they shall be drained by using the aspirator.

This aspiration work is indispensable and frequently required in a general inspection and treatment using the endoscopic system.

A conventional aspirator for the endoscopic system comprises a suction nozzle disposed at an end of an insertion portion of the endoscopic system, and a suction pump connected to the suction nozzle through a suction flask. The suction pump is continuously operated while an operator keeps a aspirator button disposed on a controlling portion turned ON, and removes obstacles such as feculence into the suction flask.

Such a conventional aspirator frequently causes a disadvantage that the suction nozzle sucks and sticks to the wall of a subject to be inspected.

The sticking to the wall not only hinders the view field of the endoscope by blocking its optical observation system with the wall, but also dangerously increases a negative pressure in the suction nozzle to perforate the wall with an edge of the endoscope if the wall is thin such as a large intestine.

Further, a conventional aspirator for the endoscopic system continues the aspirating work while its aspirator button is ON, so that an operator must alternately and intermittently push and rapidly release the button to avoid the risk of perforating the wall. Therefore, the operation is bothersome and increases fatigue of the fingers of the operator.

The present invention solves the above mentioned problems inherent to the conventional aspirator for the endoscopic system.

SUMMARY OF THE INVENTION

An object of the present invention is to provide an aspirator for an endoscopic system, which does not cause a problem of a suction nozzle sticking to a subject to be inspected.

Another object of the present invention is to provide an aspirator for an endoscopic system, which can automatically perform intermittent aspiration while an aspirator button is kept turned ON during the operation.

In order to accomplish the objects, the present invention provides an aspirator for an endoscopic system, having a suction nozzle for aspirating obstacles and disposed at an end of an endoscope, a suction pump, a suction conduit for connecting the suction nozzle to the suction pump. The aspirator further comprises an electromagnetic valve disposed in the suction conduit, and an electromagnetic valve controller. The controller controls the electromagnetic valve such that the suction conduit is closed when an aspiration command signal is not supplied from an aspirator button during the operation of the suction pump, and such that the suction conduit is alternately opened and closed when the aspiration command signal is supplied from the aspirator button during the operation of the suction pump.

BRIEF DESCRIPTION OF THE DRAWINGS

These and other objects, features and advantages of the present invention will become apparent from the following description of preferred embodiments taken in conjunction with the accompanying drawings in which.

DETAILED DESCRIPTION OF THE EMBODIMENTS

Figure 1:
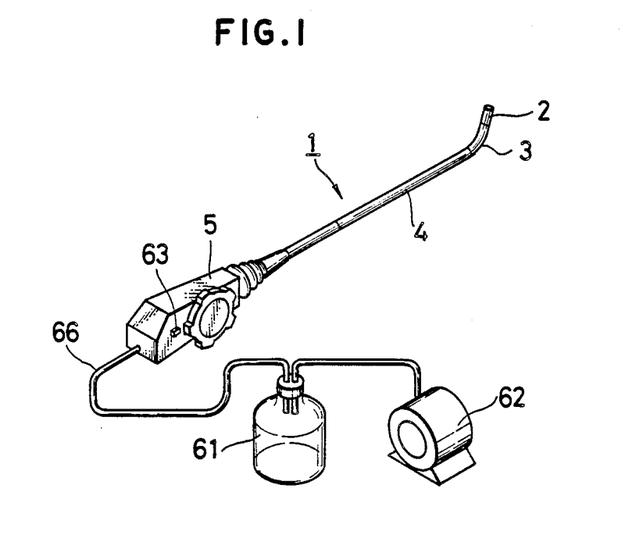
FIG. 1 is a perspective view showing the outline of an aspirator for an endoscopic system according to the present invention.

FIG. 1 is a view showing the arrangement of an aspirator for an endoscopic system according to the present invention. In the figure, an endoscope 1 comprises, from a front end to a rear end, a front end portion 2 incorporating a solid-state photographing element (hereinafter referred to as "CCD") and an optical observation system, a bending portion 3 moving up and down and left and right according to instructions from an operator, an intermediate portion 4, and a control portion 5.

The control portion 5 comprises an aspirator button 63, a controlling knob for controlling the bending portion 3, various control buttons (not shown), a power source portion (not shown), and an intermittent aspirating means to be described later. A suction conduit 66 is connected to the control portion 5.

One end of the suction conduit 66 is connected to a suction flask 61 having a suction pump 62, and the other end thereof is connected through the control portion 5 to a suction nozzle 25 (FIG. 2) disposed at the front end of the endoscope.

Figure 2:
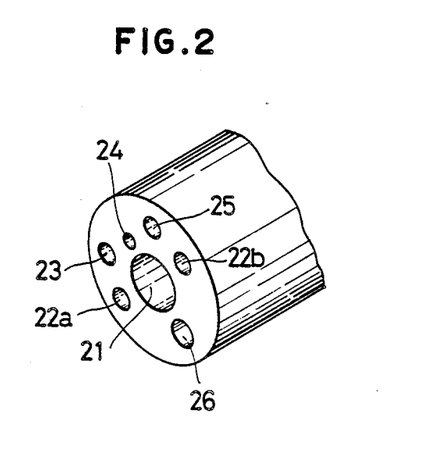
FIG. 2 is a partly enlarged perspective view showing a front end portion of the endoscope shown in FIG. 1.

As shown in FIG. 2, the front end of the endoscope comprises an optical observation system 21 including a lens window provided with the CCD, illuminating fibers 22a and 22b, a liquid feeding nozzle 23, a gas feeding nozzle 24, the suction nozzle 25, and a forceps mouth 26 used for biopsy. The liquid feeding nozzle 23 and the gas feeding nozzle 24 are used for washing and removing feculence adhered to the surface of the optical observation system 21 during the operation.

As mentioned in the above, the aspirator is provided with the intermittent aspirating means which is disposed in the middle of the suction conduit 66 in the control portion 5. The intermittent aspirating means comprises an electromagnetic valve and an electromagnetic valve controller which is arranged in a circuit for connecting the electromagnetic valve to the aspirator button of the control portion 5. While the aspirator button 63 is in an ON state, the intermittent aspirating means alternately closes and opens the electromagnetic valve automatically.

Figure 3:
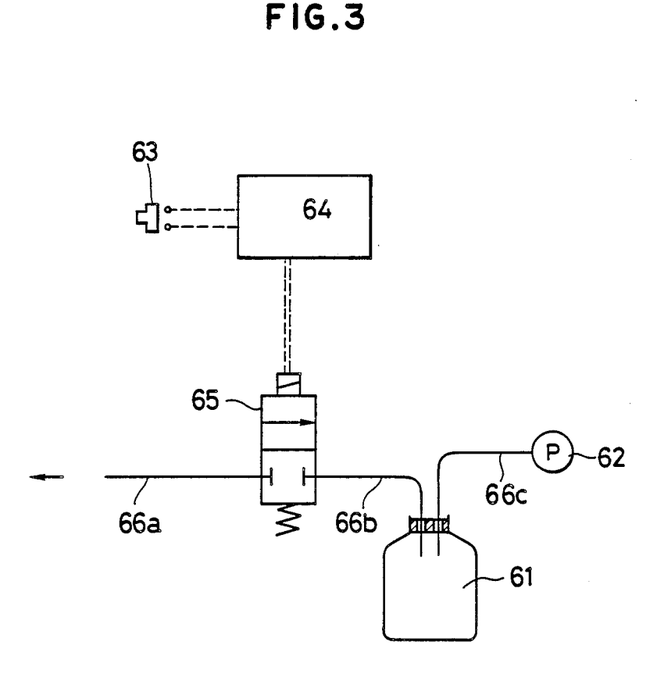
FIG. 3 is a connection diagram showing the aspirator for the endoscopic system according to the present invention.

According to the first embodiment shown in FIG. 3, an intermittent aspirating means 6 comprises an electromagnetic valve 65 and an electromagnetic valve controller 64. The electromagnetic valve 65 is disposed in the middle of the suction conduit 66 connecting the suction pump 62 and the suction flask 61 to the suction nozzle 25. The electromagnetic valve controller 64 is disposed in a circuit (indicated by dotted lines) connecting the electromagnetic valve 65 to the aspirator button 63.

The electromagnetic valve 64 has a usual circuit in which, when the aspirator button 63 is turned On to generate intermittent aspiration command signals, intermittent open/close pulses are supplied to the electromagnetic valve 65.

In the first embodiment, the controller 64 accommodates a pulse generator which is activated on receiving an ON signal from the aspirator button 63 to supply intermittent pulses with predetermined frequencies to the electromagnetic valve 65. In synchronous with the intermittent pulses, the electromagnetic valve 65 is opened and closed.

The operation of the aspirator according to the first embodiment will be described.

Firstly, the front end 2 of the endoscope 1 is inserted into a subject to be inspected. Then, the suction pump 62 is actuated by turning a main switch (not shown) ON to maintain the suction flask 61 to have a negative pressure through the suction conduit 66c.

During the operation, an operator pushes the aspirator button 63 as and when required to automatically open and close the electromagnetic valve 65 intermittently under the control of the electromagnetic valve controller 64. As a result, obstacles such as feculence around the subject can be removed through the suction conduit 66a, electromagnetic valve 65 and suction conduit 66b into the suction flask 61.

Such an intermittent aspiration will never cause the wall of the subject to the sucked suddenly that may be caused by a continuous aspirating apparatus according to the prior art. Since the risk of sucking the wall of the subject is reduced, the mental and physical loads of the operator are reduced to improve the safety in the inspection and treatment.

Depending on the condition of the subject, the open and close intervals of the electromagnetic valve 65, i.e., the frequency and width of intermittent pulses can preliminary be set in the electromagnetic controller 64. Then, the operator is only required to continuously push the aspirator button 63 to achieve an efficient aspiration and maintain a good view field in observing the subject.

The electromagnetic valve controller 64 may be a CPU incorporating RAMs and ROMs to supply intermittent pulses having various frequencies and widths to the electromagnetic valve 65.

The aspirator button 63 may be not only a push button but also a seesaw switch.

Figure 4:
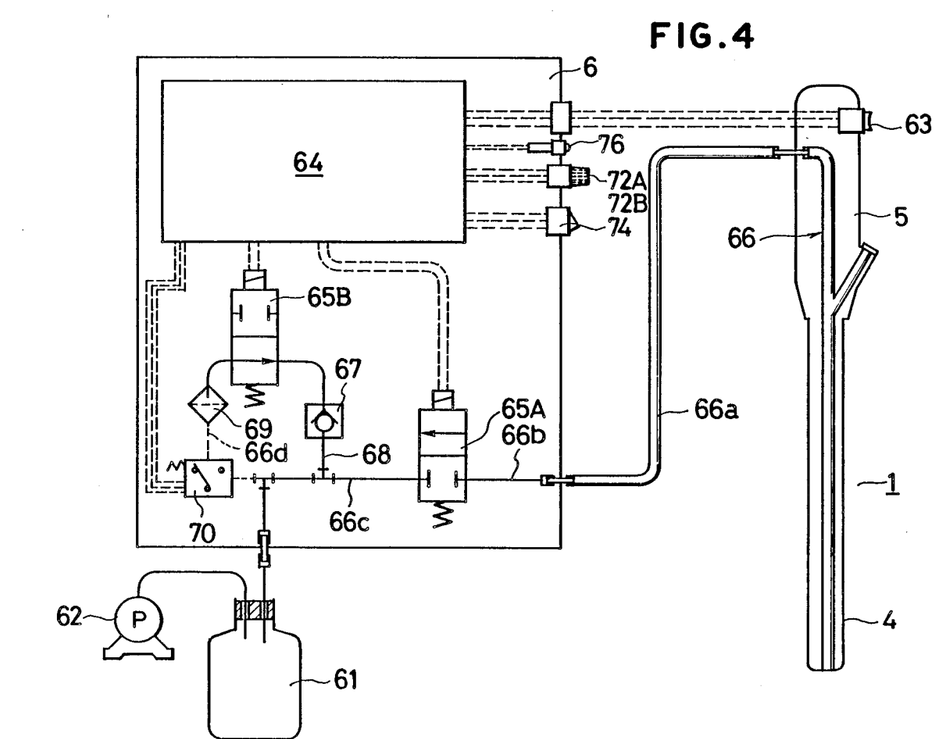
FIG. 4 is a connection diagram showing an aspirator according to a second embodiment of the present invention.

FIG. 4 is a view showing an aspirator for an endoscopic system according to the second embodiment of the present invention.

In this embodiment, an intermittent aspirating means 6 comprises a first electromagnetic valve 65A disposed in the middle of a suction conduit 66, a communicating path 68 one end thereof being connected to a suction conduit 66c between the first electromagnetic valve 65A and a suction pump 62 while the other end 66d thereof being open to atmosphere, a second electromagnetic valve 65B disposed in the communicating path 68, and a check valve 67. The intermittent aspirating means 6 further comprises an electromagnetic valve controller 64 for controlling the first and second electromagnetic valves 65A and 65B.

The electromagnetic valve controller 64 is electrically connected through circuits (indicated by dotted lines) to the first and second electromagnetic valves 65A and 65B and to an aspirator button 63. When the aspirator button 63 is turned ON, the first electromagnetic valve 65A is opened while the second electromagnetic valve 65B is alternately opened and closed.

The electromagnetic valve controller 64 further comprises two dial switches 72A and 72B for setting the operating intervals of the first and second electromagnetic valves 65A and 65B, a mode switch 74 for selecting an intermittent aspiration mode and a normal mode, and a pilot lamp 76 for indicating the intermittent aspiration mode.

Figure 5:
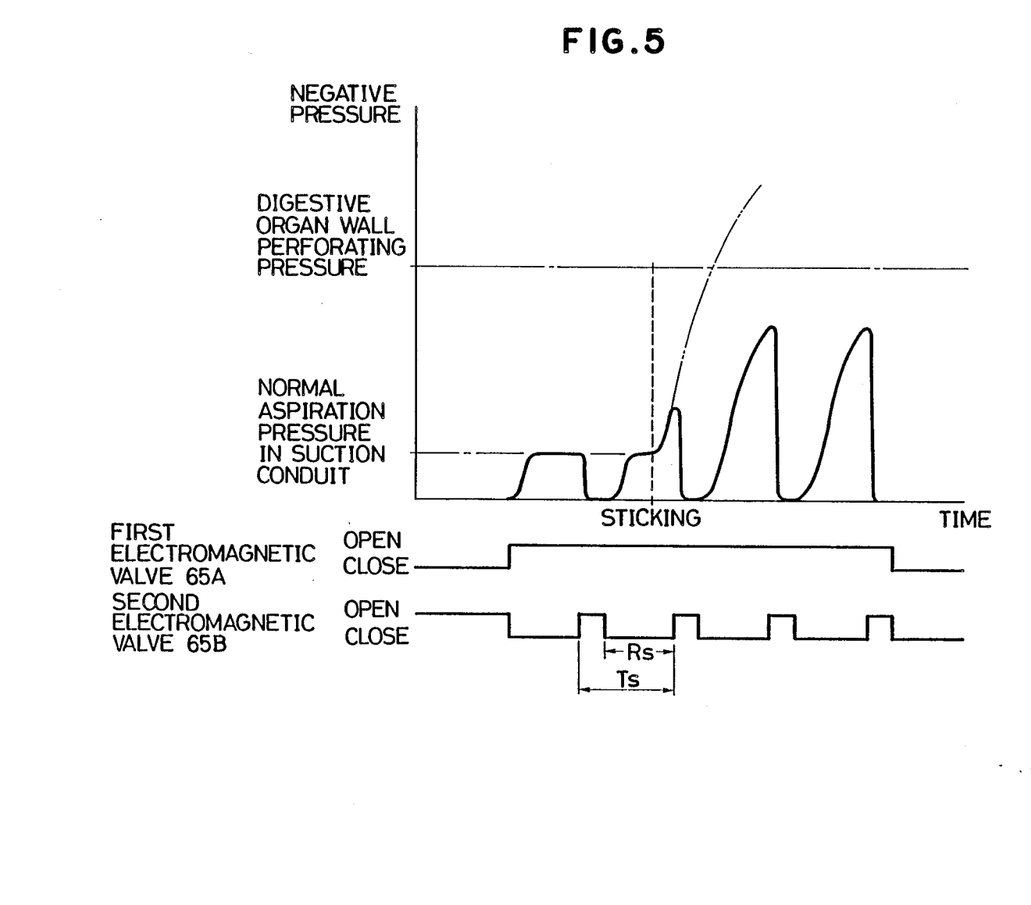
FIG. 5 is an explanatory view showing a pressure state in the suction conduit according to the second embodiment shown in FIG. 4.

According to the second embodiment, if a suction nozzle disposed at a front end of an endoscope is stuck to the wall of a subject to be inspected, a pressure state in the suction conduit will change as shown in FIG. 5.

As shown in the figure, when the first electromagnetic valve 65A is opened and the second electromagnetic valve 65B kept closed, the aspiration is continued in a manner similar to that of the prior art so that, if the nozzle 25 stuck to the wall of the subject, a negative pressure in the suction nozzle 25 is increased due to the continuous operation of the suction pump 62. If this stuck state is left as it is, the negative pressure will follow a dot and dash line in the figure to cause the risk of perforating the wall of the subject.

However, according to the intermittent aspiration mode of the second embodiment, the electromagnetic valve controller 64 controls, while the aspirator button 63 is turned ON, the first electromagnetic valve 65A to continuously be opened and the second electromagnetic valve 65B to be opened and closed alternately. When the second electromagnetic valve 65B is opened, the suction conduit 66 communicates with atmosphere through the communicating path 68 so that the negative pressure in the suction conduit 66 rapidly decreases.

After that, when the second electromagnetic valve 65B is closed, the negative pressure in the suction conduit 66 again increases. By properly selecting the intervals of opening and closing the second electromagnetic valve 65B in advance through the dial switch 72B, the negative pressure in the suction conduit 66 can be suppressed to a low level which will not cause a perforation on the wall of the subject.

As shown in FIG. 5, the cycle Ts and width Rs of an intermittent pulse are set as follows with the diameter of the suction nozzle 25 being 2.7 mm.

$$0.2 < Rs/Ts \leq 0.6$$

$$Ts \leq 0.6 \text{ (sec)}$$

In the second embodiment, the electromagnetic valve controller 64 comprises a CPU which receives command signals from the mode switch 74 and dial switches 72A and 72B and supplies driving pulses to the first and second electromagnetic valves 65A and 65B.

In FIG. 4, there are disposed an air filter 69 and a pressure switch 70 in the communicating path 66c and 66d.

Further, in the second embodiment shown in FIG. 4, a shutoff valve such as a normal mechanical valve may substitute for the first electromagnetic valve 65A.

Figure 6:
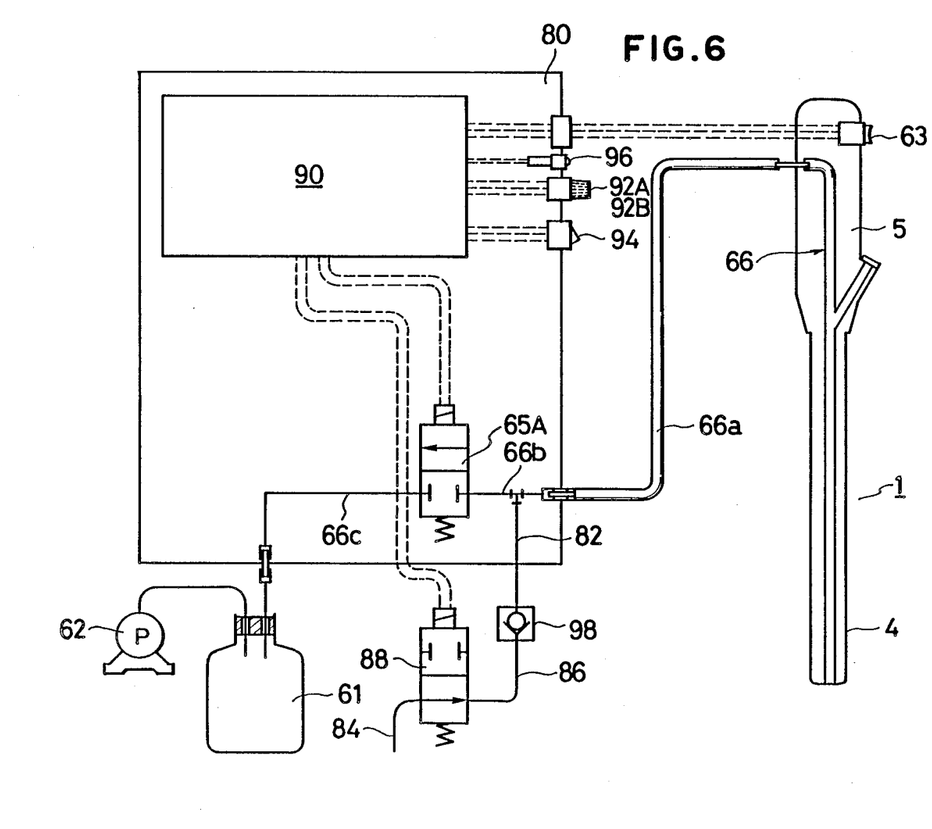
FIG. 6 is a connection diagram showing an aspirator according to a third embodiment of the present invention.

FIG. 6 is a view showing an aspirator for an endoscopic system according to the third embodiment of the present invention.

In this embodiment, an intermittent aspirating means 80 comprises a first electromagnetic valve 65A disposed in the middle of a suction conduit 66, a communicating path 86 one end 82 thereof being connected to a suction conduit 66b between the first electromagnetic valve 65A and a controlling portion 5 while the other end 84 thereof being open to atmosphere, and a second electromagnetic valve 88 disposed in the communicating path 86. The intermittent aspirating means 80 further comprises an electromagnetic valve controller 90 for controlling the first and second electromagnetic valves 65A and 88. The electromagnetic valve controller 90 is electrically connected through circuits indicated by dotted lines to the first and second electromagnetic valves 65A and 88 and to an aspirator button 63 such that, while the aspirator button 63 is in an ON state, the first and second electromagnetic valves 65A and 88 are intermittently and alternately opened and closed.

The electromagnetic valve controller 90 comprises two dial switches 92A and 92B for setting the operating intervals of the first and second electromagnetic valves 65A and 88, a mode switch 94 for selecting an intermittent aspirating mode and a normal mode, and a pilot lamp 96 for indicating the intermittent aspirating mode.

The communicating path 86 is provided with a check valve 98.

The operation of the third embodiment will be described with reference to FIG. 7.

In the intermittent aspirating mode, the electromagnetic valve controller 90 controls, while the aspirator button 63 is in an ON state, the first electromagnetic valve 65A to be opened and closed intermittently with predetermined intervals and the second electromagnetic valve 88 to be opened and closed intermittently in a manner opposite to the operation of the first electromagnetic valve 65A. Namely, when the first electromagnetic 65A is opened, the second electromagnetic valve 88 is closed so that the aspiration is carried out through the first electromagnetic valve 65A. If a suction nozzle located at a front end of the endoscope is stuck to the wall of the subject, a negative pressure in the suction conduit 66 is increased. However, the first electromagnetic valve 65A is soon closed, and the second electromagnetic valve 88 is opened. Therefore, the suction conduit 66b is disconnected from the suction conduit 66c to stop the aspiration. The suction conduit 66 is connected to the atmosphere through the communicating path 86 so that the negative pressure in the suction conduit 66 rapidly decreases. Therefore, according to the third embodiment, the negative pressure in the suction conduit 66 can be suppressed to a level lower than a sticking pressure (pressure at which the sticking is caused) as shown in FIG. 7.

Figure 7:
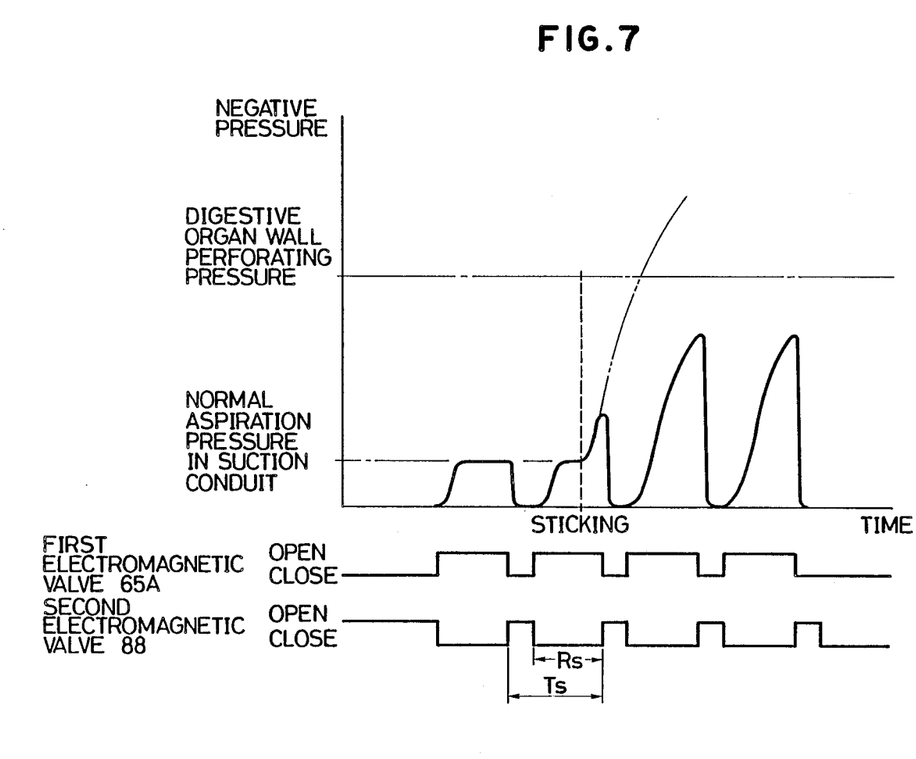
FIG. 7 is an explanatory view showing a pressure state in the suction conduit according to the third embodiment shown in FIG. 6.

In FIG. 7, the cycle Ts and with Rs of an intermittent pulse is set as follows with the diameter of the suction nozzle 25 being 2.7 mm.

$$0.2 < Rs/Ts \leq 0.6$$

$$Ts \leq 0.6 \text{ (sec)}$$

In the third embodiment, the electromagnetic valve controller 90 comprises a CPU which receives command signals from the mode switch 94 and the dial switches 92A and 92B, and supplies driving pulses to the first and second electromagnetic valves 65A and 88.

Figure 8:
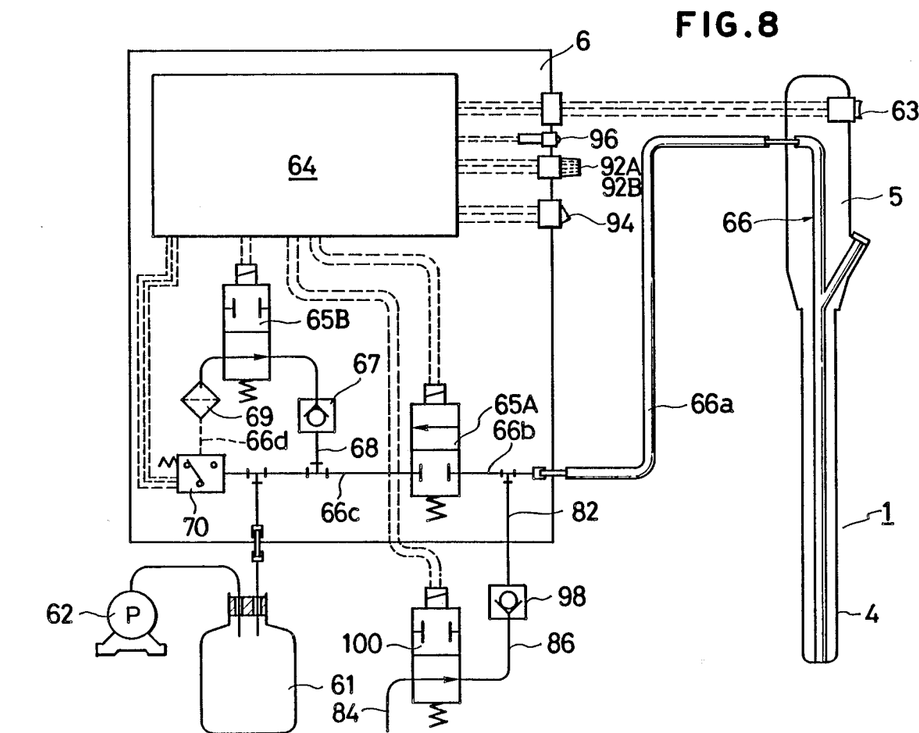
FIG. 8 is a connection diagram showing an aspirator according to a fourth embodiment of the present invention.

FIG. 8 is a view showing an aspirator for an endoscopic system according to the fourth embodiment of the present invention.

This embodiment is a combination of the second embodiment and the third embodiment both mentioned in the above. An intermittent aspirating means of the fourth embodiment comprises a first electromagnetic valve 65A disposed in the middle of a suction conduit 66, a second electromagnetic valve 65B disposed in a communicating path 68, and a third electromagnetic valve 100 disposed in a communicating path 86. Other elements of this embodiment are the same as those of the second and third embodiments, so any explanation thereof will be omitted.

Figure 9:
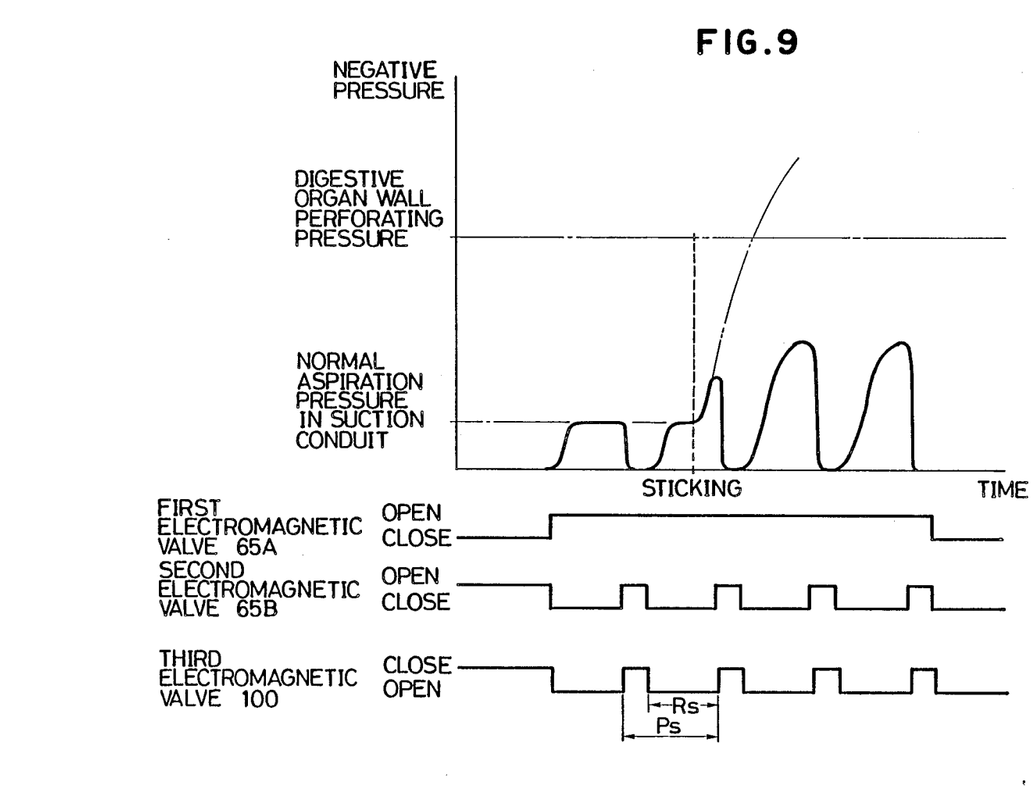
FIG. 9 is an explanatory view showing a pressure state in the suction conduit according to the fourth embodiment shown in FIG. 8.

The operation of the fourth embodiment is shown in FIG. 9, while the first electromagnetic valve 65A is opened, the second and third electromagnetic valves 65B and 100 are opened and closed intermittently. According to the fourth embodiment, a negative pressure in the suction conduit 66 is reduced by the two electromagnetic valves 65B and 100 so that the negative pressure can surely be suppressed to a lower level.

In summary, the aspirator for an endoscopic system according to the present invention comprises an intermittent aspirating means disposed in the middle of a suction conduit connecting a suction nozzle to a suction flask, the intermittent aspirating means being able to intermittently open and close the suction conduit automatically while an aspirator button is in an ON state. Therefore, without operating the aspirator button intermittently, the intermittent aspiration can be realized only by turning the aspirator button ON so that an operation's load can greatly be reduced.

Therefore, according to the aspirator of the present invention, inspection and treatment by the endoscopic system can surely be carried out efficiently without causing fatigue on the operator and sucking the wall of a subject to be inspected.

Various modifications will become possible for those skilled in the art after receiving the teachings of the present disclosure without departing from the scope thereof.

What is claimed is:

1. An aspirator system for an endoscope, comprising:
an endoscope having an aspirating suction nozzle at its insertion end;
a suction pump;
a suction conduit connecting the suction nozzle to the suction pump;
intermittent aspirating means for alternately opening and closing the suction conduit during operation of the suction pump to carry out intermittent aspiration; and
an aspirator button for supplying an aspiration command signal to the intermittent aspiration means;
the intermittent aspirating means comprising:
  (a) a first electromagnetic valve disposed in the suction conduit;
  (b) a communicating path connected at one end to the suction conduit between the first electromagnetic valve and the suction pump, the other end of the path being open to atmosphere;
  (c) a second electromagnetic valve disposed in the communicating path; and
  (d) an electromagnetic valve controller means, for controlling the first electromagnetic valve to close the suction conduit when the aspiration command signal is not supplied from the aspirator button during operation of the suction pump, but controlling the first and second electromagnetic valves to open the suction conduit and alternately open and close the communicating path when the aspiration command signal is supplied by the aspirator during operation of the suction pump.

2. An aspirator system for an endoscope, comprising:
a suction nozzle disposed at the insertion end of the endoscope for aspirating obstacles;
a suction pump;
a suction conduit for connecting the suction nozzle to the suction pump;
intermittent aspirating means for automatically and alternately opening to atmosphere and closing the suction conduit during operation of the suction pump to carry out intermittent aspiration;
and an aspirator button for supplying an aspiration command signal to said intermittent aspirator means the aspirator button being electrically connected to said intermittent aspirating means;
wherein said intermitten aspirating means comprises:
a first electromagnetic valve disposed in the suction conduit;
a communicating path, one end thereof being connected to the suction conduit between the first electromagnetic valve and the suction nozzle, the other end thereof being open to atmosphere;
a second electromagnetic valve disposed in the communicating path; and
an electromagnetic valve controller means for controlling the first electromagnetic valve so as to close the suction conduit when the aspiration command signal is not supplied from the aspirator button during operation of the suction pump, and controlling the first and second electromagnetic valves to alternately open and close the suction conduit and the communicating path in opposite phase with each other when the aspiration command signal is supplied from the aspirator button during operation of the suction pump.

* * * * *